(12) United States Patent
Safai

(10) Patent No.: US 11,852,620 B2
(45) Date of Patent: *Dec. 26, 2023

(54) SYSTEM AND METHOD FOR EVALUATING A BOND

(71) Applicant: The Boeing Company, Chicago, IL (US)

(72) Inventor: Morteza Safai, Newcastle, WA (US)

(73) Assignee: THE BOEING COMPANY, Arlington, VA (US)

(*) Notice: Subject to any disclaimer, the term of this patent is extended or adjusted under 35 U.S.C. 154(b) by 105 days.

This patent is subject to a terminal disclaimer.

(21) Appl. No.: 17/451,290

(22) Filed: Oct. 18, 2021

(65) Prior Publication Data
US 2022/0034861 A1  Feb. 3, 2022

Related U.S. Application Data

(63) Continuation of application No. 16/670,857, filed on Oct. 31, 2019, now Pat. No. 11,181,518.

(51) Int. Cl.
G01N 33/207 (2019.01)
G01N 29/04 (2006.01)
H05H 1/24 (2006.01)

(52) U.S. Cl.
CPC ......... G01N 33/207 (2019.01); G01N 29/043 (2013.01); H05H 1/2406 (2013.01); G01N 2291/267 (2013.01)

(58) Field of Classification Search
CPC ............... G01N 33/207; G01N 29/043; G01N 29/0654; G01N 29/04; G01N 29/2431; G01N 2203/001; G01N 2203/0296; G01N 2291/1267; G01N 2203/0658; G01N 2291/0057; G01N 2291/001; G01N 2291/0231; G01N 2203/005; H05H 1/2406; H05H 1/2439; H05H 1/48; G01M 7/08

USPC .......................................................... 73/588
See application file for complete search history.

(56) References Cited

U.S. PATENT DOCUMENTS

| | | | |
|---|---|---|---|
| 5,770,831 A | 6/1998 | Kaneko et al. | |
| 7,075,162 B2* | 7/2006 | Unger | F16K 99/0059 257/419 |
| 8,008,835 B2* | 8/2011 | Degertekin | B06B 1/0292 310/309 |
| 8,132,460 B1 | 3/2012 | Toller et al. | |
| 9,625,425 B2* | 4/2017 | Stewart | G01N 3/00 |
| 10,210,740 B2* | 2/2019 | Ihn | G08B 21/18 |

(Continued)

OTHER PUBLICATIONS

Bossi et al., "Laser Bond Inspection for Adhesive Bond Strength," SAMPE, Long Beach, CA, 2011, pp. 1-10.

(Continued)

*Primary Examiner* — Jacques M Saint Surin
(74) *Attorney, Agent, or Firm* — MH2 Technology Law Group LLP

(57) ABSTRACT

A system for evaluating a bond includes a first electrode and a second electrode that are spaced apart from one another. The system also includes a sacrificial material layer positioned proximate to a surface of a bonded structure that includes the bond. The system also includes a power source configured to cause the first and second electrodes to generate an electrical arc that at least partially ablates the sacrificial material layer as part of a non-destructive inspection of the bond.

20 Claims, 2 Drawing Sheets

(56) References Cited

U.S. PATENT DOCUMENTS

| | | |
|---|---|---|
| 11,053,672 B2 * | 7/2021 | Locco .................... E03C 1/324 |
| 11,181,518 B2 * | 11/2021 | Safai ....................... H05H 1/48 |
| 2002/0037218 A1 | 3/2002 | Webster |
| 2013/0022752 A1 | 1/2013 | Antonakas |
| 2015/0128717 A1 | 5/2015 | May et al. |
| 2019/0170700 A1 | 6/2019 | Clemen, Jr. et al. |
| 2019/0259579 A1 | 8/2019 | Takamatsu et al. |
| 2019/0300159 A1 | 10/2019 | Kikuchi et al. |

OTHER PUBLICATIONS

Richards, Joanna (Authorized PCT officer), PCT International Search Report and Written Opinion dated Jan. 25, 2021 in corresponding PCT Application No. PCT/US2020/055038, 12 pages.

Kalms et al., "Assessment of bond defects in adhesive joints before and after the treatment with laser generated shock waves," Proc. of SPIE, vol. 9063, pp. 906327-1 through 906327-11.

Kobayashi, Miki (Authorized PCT officer), International Preliminary Report on Patentability dated May 3, 2022 in corresponding PCT Application No. PCT/US2020/055038, 9 pages.

* cited by examiner

SYSTEM AND METHOD FOR EVALUATING A BOND

CROSS-REFERENCE TO RELATED APPLICATIONS

This application is a continuation application of, and claims priority to, U.S. patent application Ser. No. 16/670,857, filed Oct. 31, 2019, the disclosure of which is hereby incorporated herein by reference in its entirety.

FIELD OF THE DISCLOSURE

The present disclosure is directed to systems and methods for evaluating a bond between two components. More particularly, the present disclosure is directed to systems and methods for evaluating an adhesive bond between two components using a plasma actuator.

BACKGROUND

Laser bond inspection (LBI) is a process that is used to evaluate an adhesive bond in a bonded structure. LBI uses a laser pulse to create a plasma, which generates stress waves in the bonded structure. In an example, the bonded structure includes carbon fiber reinforced polymer (CFRP)-to-CFRP or CFRP-to-metal. The stress waves mechanically create a tension load on the adhesive bond. During exposure to this load, a weak joint will fail, and a strong joint will not. Bonded structures with weak joints are thus be identified and repaired or discarded. However, current LBI systems are large and expensive. Therefore, what is needed is an improved system and method for evaluating a bond.

SUMMARY

A system for evaluating a bond is disclosed. The system includes a first electrode and a second electrode that are spaced apart from one another. The system also includes a sacrificial material layer positioned proximate to a surface of a bonded structure that includes the bond. The system also includes a power source configured to cause the first and second electrodes to generate an electrical arc that at least partially ablates the sacrificial material layer as part of a non-destructive inspection of the bond.

In another implementation, the system includes a first electrode and a second electrode. The system also includes a dielectric material layer positioned at least partially between the first electrode and the second electrode, such that the second electrode is not in contact with the first electrode. The system also includes a sacrificial material layer positioned in contact with a surface of a bonded structure that includes the bond. The sacrificial material layer is positioned on a same side of the dielectric material layer as the second electrode and a different side of the dielectric material layer than the first electrode. The system also includes a power source configured to transmit an alternating current pulse to the first and second electrodes, which causes the first and second electrodes to generate an electrical arc that at least partially ablates a sacrificial material layer to generate a plasma. The generation of the plasma generates a first wave that is directed into the bonded structure. The first wave reflects off of the bond in the bonded structure as a second wave.

A method for evaluating a bond is also disclosed. The method includes placing a sacrificial material layer on a surface of a bonded structure. The method also includes generating an electrical arc to least partially ablate the sacrificial material layer, which generates a first wave that is directed into the bonded structure, wherein the first wave reflects off of the bond in the bonded structure as a second wave.

It is to be understood that both the foregoing general description and the following detailed description are exemplary and explanatory only and are not restrictive of the present teachings, as claimed.

BRIEF DESCRIPTION OF THE DRAWINGS

The accompanying drawings, which are incorporated in and constitute a part of this specification, illustrate aspects of the present teachings and together with the description, serve to explain the principles of the present teachings.

Figure 1:
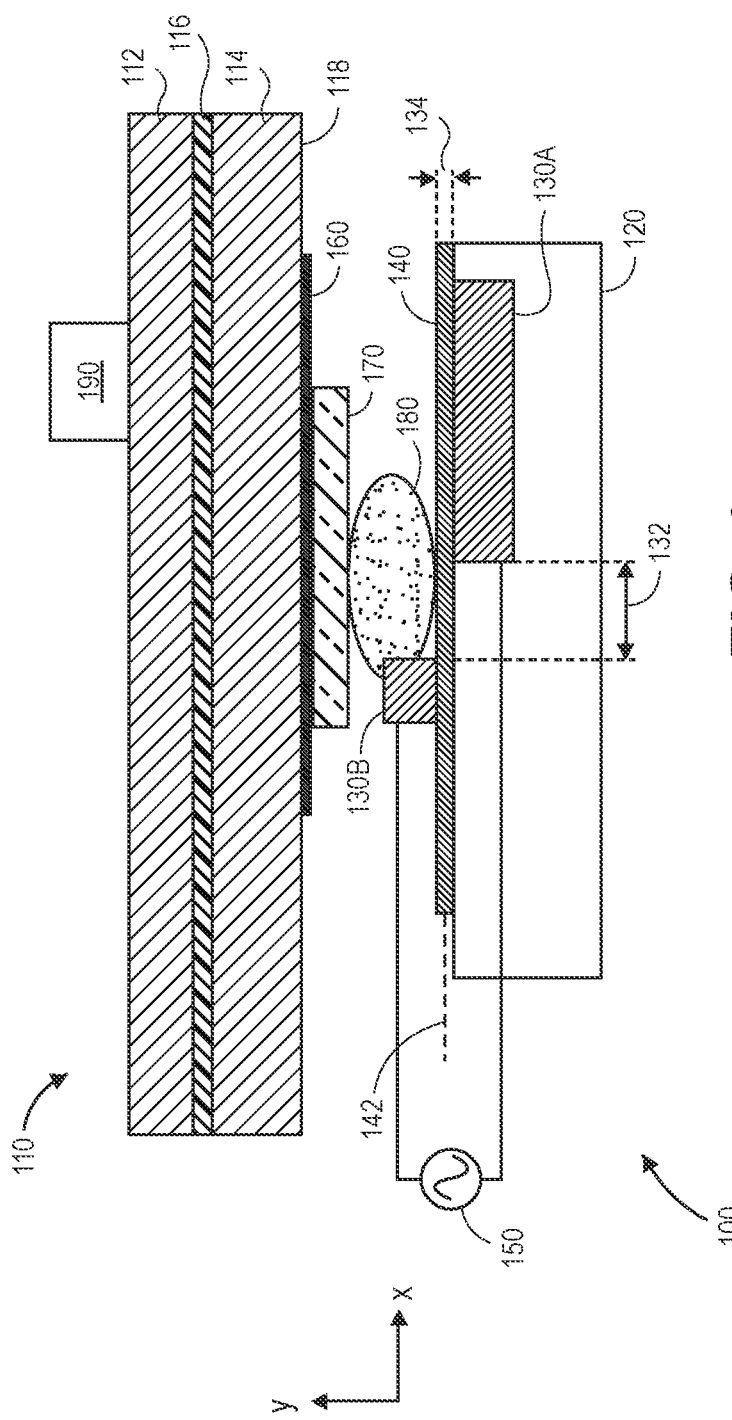
FIG. 1 illustrates a schematic view of a system for evaluating a bond in a bonded structure, according to an implementation.

It should be noted that some details of the figures have been simplified and are drawn to facilitate understanding rather than to maintain strict structural accuracy, detail, and scale.

DESCRIPTION

Reference will now be made in detail to the present teachings, examples of which are illustrated in the accompanying drawings. In the drawings, like reference numerals have been used throughout to designate identical elements. In the following description, reference is made to the accompanying drawings that form a part thereof, and in which is shown by way of illustration specific examples of practicing the present teachings. The following description is, therefore, merely exemplary.

The present disclosure is directed to a plasma actuator that represents a smaller, less expensive alternative to LBI systems. The plasma actuator includes a support, one or more electrodes, and a dielectric material layer. The plasma actuator is configured to generate an electrical arc that at least partially ablates a sacrificial material layer to create a plasma, which generates the waves that travel into the bonded structure to evaluate a quality of the bond, as described in greater detail below.

FIG. 1 illustrates a schematic view of a system 100 for evaluating a bond in a bonded structure 110, according to an implementation. The system 100 includes a plasma actuator that provides an alternative to LBI systems. Thus, the system 100 evaluates the bond (e.g., assists in determining a quality of the bond) in the bonded structure 110 without use of a laser. More particularly, the system 100 applies a predetermined force to the bond. The predetermined force is from about 30% to about 70% (e.g., about 50%) of the force required to break an ideal bond. The bond is then inspected. If the bond is not fractured or broken, the bond is passing/satisfactory. If the bond is fractured or broken, the bond is not passing/not satisfactory.

The bonded structure 110 includes a first component 112 and a second component 114 that are bonded together by a bond material 116 (e.g., the bond). As will be appreciated, there may be more components that are bonded together, but for simplicity, only two components are illustrated. In an example, the first and second components 112, 114 are made at least partially from CFRP. In another example, the first component 112 is made at least partially from CFRP, and the second component 114 is made at least partially from metal. The bond material 116 can be a resin, an adhesive, or an epoxy (e.g., boron epoxy or carbon epoxy).

The system 100 includes a support 120. The support 120 may also be referred to as a support surface or a substrate. The support 120 can be or include a polyimide material, a polyamide material, or both. In an example, the support 120 is made at least partially from a polyamide tape such as KAPTON® tape. The support 120 provides high heat-resistance and high dielectric strength. The support 120 also prevents unintended dielectric arcs.

The system 100 also includes one or more electrodes (two are shown: a first electrode 130A and a second electrode 130B). The first and second electrodes 130A, 130B are configured to generate an electrical arc, as described in greater detail below.

The first and second electrodes 130A, 130B are made at least partially from copper or other metals. The electrical arc at least partially depends upon the material(s) in the first and second electrodes 130A, 130B. For example, the material(s) can affect the magnitude, direction, and/or temperature of the electrical arc.

In one implementation, the first and second electrodes 130A, 130B are the same size (e.g., length, width, and/or height). However, in the implementation shown in FIG. 1, the first electrode 130A has a different size (e.g., a different length) than the second electrode 130B. For example, the first electrode 130A can have a length from about 10 mm to about 30 mm (e.g., 20 mm), and the second electrode 130B can have a length from about 1 mm to about 10 mm (e.g., 5 mm). The electrical arc at least partially depends upon the sizes (e.g., lengths) of the first and second electrodes 130A, 130B. The sizes (e.g., lengths) affect the magnitude, direction, and/or temperature of the electrical arc. As the size(s) of the electrodes(s) 130A, 130B increase(s), the amount of electrical current required to generate the electrical arc also increases. Larger electrical arcs have higher temperatures.

The first and second electrodes 130A, 130B are spaced apart from one another. As shown, the first and second electrodes 130A, 130B can be spaced apart from one another by a first distance 132 in a first direction that is substantially parallel to a surface 118 of the bonded structure 110. The first and second electrodes 130A, 130B can also be spaced apart from one another by a second distance 134 in a second direction that is substantially perpendicular to the surface 118 of the bonded structure 110. The first distance 132 can be from about 2 mm to about 10 mm (e.g., about 5 mm), and the second distance 134 can be from about 0.5 mm to about 2 mm (e.g., about 1 mm). Thus, as shown, the first electrode 130A is positioned farther from the bonded structure 110 than the second electrode 130B. The electrical arc at least partially depends upon the spacing/positioning of the first and second electrodes 130A, 130B with respect to one another. For example, the spacing/positioning affects the magnitude, direction, and/or temperature of the electrical arc. Moving the first and second electrodes 130A, 130B closer together reduces the size of the electrical arc, which reduces the temperature of the electrical arc. Conversely, moving the first and second electrodes 130A, 130B farther apart increases the size of the electrical arc, which increases the temperature of the electrical arc.

The system 100 also includes a dielectric material layer 140 positioned at least partially between the first and second electrodes 130A, 130B. The first direction (referenced above) may be substantially parallel to a plane 142 through the dielectric material layer 140, and the second direction may be substantially perpendicular to the plane 142. The plane 142 may also be substantially parallel to the surface 118 of the bonded structure 110. The dielectric material layer 140 can have a thickness from about 0.5 mm to about 3 mm (e.g., about 1 mm). The dielectric material layer 140 can be or include a polyimide film with a silicone adhesive, such as KAPTON® tape. In other implementations, the dielectric material layer 140 is made at least partially from polytetrafluoroethylene (PTFE). For example, the dielectric material layer 140 can be made from TEFLON®. The dielectric material layer 140 is configured to provide an electrical barrier between the first and second electrodes 130A, 130B. As the thickness and/or resistance of the dielectric barrier increases, more electrical current is needed to generate the electrical arc. Conversely, as the thickness and/or resistivity of the dielectric barrier decreases, less electrical current is needed to generate the electrical arc.

As shown, the first electrode 130A is in contact with and/or coupled to the support 120 and/or the dielectric material layer 140. The second electrode 130B is in contact with and/or coupled to the dielectric material layer 140, but not in contact with and/or coupled to the support 120. The dielectric material layer 140 is in contact with and/or coupled to the support 120, the first electrode 130A, the second electrode 130B, or a combination thereof.

The system 100 includes a power source 150 that is connected to the first and second electrodes 130A, 130B. The power source 150 can have a voltage from about 40 kilovolts (kV) to about 60 kV. The power source 150 generates an alternating current (AC) pulse having a duration from about 10 nanoseconds (ns) to about 1 millisecond (ms), about 25 ns to about 500 ns, or about 50 ns to about 200 ns. For example, the pulse can have a duration of about 100 ns. The pulse causes the first and second electrodes 130A, 130B to generate the electrical arc.

A sacrificial material layer 160 is coupled to and/or in contact with the surface 118 of the bonded structure 110. The sacrificial material layer 160 is made from a material that is configured to be at least partially ablated by the electrical arc to generate a plasma. For example, the sacrificial material layer 160 can be made at least partially from a polyvinyl chloride tape.

A liquid (e.g., water or FLUORINERT®) 170 is positioned at least partially between the surface 118 of the bonded structure 110 and the dielectric material layer 140. As shown, the liquid 170 is positioned on the sacrificial material layer 160. As described in greater detail below, the ablation of the sacrificial material layer 160 generates a compression wave, and the liquid 170 directs at least a portion of the compression wave into the bonded structure 110 (e.g., toward the bond material 116).

Figure 2:
FIG. 2 illustrates a flowchart of a method for evaluating the bond in the bonded structure, according to an implementation.

FIG. 2 illustrates a flowchart of a method 200 for evaluating the bond in the bonded structure 110, according to an implementation. The method 200 may be performed using the system 100. An illustrative order of the method 200 is described below; however, it will be appreciated that one or more steps of the method 200 may be performed in a different order and/or omitted.

The method 200 includes placing the sacrificial material layer 160 on the surface 118 of the bonded structure 110, as at 202. In an example, the sacrificial material layer 160 is adhered to the surface 118. The method 200 also includes placing the liquid 170 between the system 100 and the sacrificial material layer 160, as at 204. In an example, the liquid is placed on the sacrificial material layer 160.

The method 200 includes generating an electrical pulse using the system 100, as at 206. More particularly, the power source 150 is connected to the electrodes 130A, 130B and transmits an electrical (e.g., AC) pulse to the electrodes 130A, 130B, which causes the electrodes 130A, 130B to generate the electrical arc. The electrical arc least partially ablates at least a portion of the sacrificial material layer 160 to generate a plasma 180 (see FIG. 1). Thus, the plasma 180 can be generated without the user of a laser, which allows the system 100 to have a smaller footprint and be less expensive than conventional LBI systems.

A first wave is generated in response to the ablation of the sacrificial material layer 160 and/or the generation of the plasma 180. The first wave is a compression wave. The first wave is directed toward the surface 118 of the bonded structure 110 (e.g., toward the bond material 116) at least partially by the liquid 170. The first wave can also or instead be directed toward the surface 118 of the bonded structure 110 (e.g., toward the bond material 116) at least partially in response to the material of the electrodes 130A, 130B, the size of the electrodes 130A, 130B, the positioning of the electrodes 130A, 130B, the positioning of the dielectric material layer 140, or a combination thereof. The first wave reflects off of the bonded structure 110. More particularly, the first wave reflects off of the bond material 116 and/or the surface 118 as a second wave. The second wave is a tension wave.

The first wave and/or the second wave may apply a predetermined force to the bond (e.g., bond material 116). The predetermined force is from about 30% to about 70% (e.g., about 50%) of the force required to break an ideal bond.

The method 200 also includes inspecting the bonded structure 110, as at 208. For example, the bond (e.g., bond material 116) can be inspected with a non-destructive inspection (NDI) system 190 (see FIG. 1) such as an ultrasound imaging system or an ultrasonic inspection system after the first wave reflects off of the bond material 116 to form the second wave. The inspection detects inconsistencies and/or damage to the bond that occur(s) in response to the contact with the first wave and/or the second wave. If the inspection reveals that the bond (e.g., bond material 116) is fractured or broken, then the quality of the bond is determined to be bad (i.e., the bond did not pass inspection). If the inspection reveals that the bond (e.g., bond material 116) is not fractured or broken, then the quality of the bond is determined to be good (i.e., the bond passes inspection).

In other implementations, one or more portions of the system 100 can be replaced or modified to generate different pulse widths, electrical arcs with different properties, waves with different properties, or a combination thereof. For example, one or both of the electrodes 130A, 130B can be replaced with different electrode(s) that are made of a different material and/or have a different size/shape. In addition, the positioning of the electrodes 130A, 130B (e.g., the spacing between the electrodes 130A, 130B) can be varied. In another example, the dielectric material layer 140 can be replaced with a different dielectric material layer that is made of a different material and/or has a different shape/size. In addition, the positioning of the dielectric material layer 140 can be varied. Replacing or modifying the electrodes 130A, 130B and/or the dielectric material layer 140 as described above affects the magnitude, direction, and/or temperature of the electrical arc. For example, the dielectric material layer 140 can be replaced with a second dielectric material layer having a different thickness and/or resistivity, which affects the amount of electrical current needed to generate the electrical arc and/or the temperature of the electrical arc.

In at least one implementation, the system 100 may not include/use inspection tape with copper traces, as is oftentimes used by LBI systems, because the system 100 does not include an electromagnetic transducer (EMAT) to translate the compression wave and/or the tension wave. Indeed, the system does not receive the compression wave.

The foregoing system 100 and method 200 can replace peel ply tests, which use mechanically applied stress to pull a bond apart. The foregoing system 100 and method 200 can also replace LBI tests, which use a laser to generate the plasma and the compression wave.

The tensile force needed to damage or break a bond with a satisfactory/passing quality may be known prior to performing the method 200. Thus, the waves generated during the testing can have a force that is less than the force needed to break the bond (e.g., between about 50% and about 70% of the force). If the inspection shows that the bond is still intact after the wave(s) contact the bond, then the bond is considered to have the desired quality (the bond passes the test). If the inspection shows that the bond is damaged or broken after the wave(s) contact the bond, then the bond is not considered to have the desired quality (the bond fails the test).

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein.

While the present teachings have been illustrated with respect to one or more implementations, alterations and/or modifications can be made to the illustrated examples without departing from the spirit and scope of the appended claims. In addition, while a particular feature of the present teachings may have been disclosed with respect to only one of several implementations, such feature may be combined with one or more other features of the other implementations as may be desired and advantageous for any given or particular function. As used herein, the terms "a", "an", and "the" may refer to one or more elements or parts of elements. As used herein, the terms "first" and "second" may refer to two different elements or parts of elements. As used herein, the term "at least one of A and B" with respect to a listing of items such as, for example, A and B, means A alone, B alone, or A and B. Those skilled in the art will recognize that these and other variations are possible. Furthermore, to the extent that the terms "including," "includes," "having," "has," "with," or variants thereof are used in either the detailed description and the claims, such terms are intended to be inclusive in a manner similar to the term "comprising." Further, in the discussion and claims herein, the term "about" indicates that the value listed may be somewhat altered, as long as the alteration does not result in nonconformance of the process or structure to the intended purpose described herein. Finally, "exemplary" indicates the description is used as an example, rather than implying that it is an ideal.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompasses by the following claims.

What is claimed is:

1. A system for evaluating a bond, comprising:
 a first electrode;
 a second electrode spaced apart from the first electrode;
 a sacrificial material layer positioned proximate to a surface of a bonded structure that includes the bond; and
 a power source configured to cause the first and second electrodes to generate an electrical arc that at least partially ablates the sacrificial material layer as part of a non-destructive inspection of the bond, wherein a first wave is generated in response to the ablation of the sacrificial material layer, and wherein the first wave reflects off of the bond as a second wave.

2. The system of claim 1, further comprising an ultrasound imaging system configured to inspect the bond after the first wave reflects off of the bond.

3. The system of claim 1, wherein the first wave comprises a compression wave, and the second wave comprises a tension wave.

4. The system of claim 1, further comprising a dielectric material layer positioned at least partially between the first and second electrodes.

5. The system of claim 4, wherein a plasma is generated in response to the ablation of the sacrificial material layer, and wherein the plasma is positioned at least partially between the dielectric material layer and the sacrificial material layer.

6. The system of claim 4, further comprising a support including a polyimide material, a polyamide material, or both, wherein the first electrode is in contact with the support, wherein the dielectric material layer is in contact with the support, and wherein the second electrode is not in contact with the support.

7. The system of claim 1, wherein the power source is configured to transmit an alternating current pulse having a duration from about 50 ns to about 200 ns to the first and second electrodes, which causes the first and second electrodes to generate the electrical arc.

8. The system of claim 1, wherein the first electrode is spaced apart from the second electrode by a first distance in a first direction, wherein the first distance is from about 0.5 mm to about 2 mm, and wherein the first direction is substantially parallel to a plane through the dielectric material layer.

9. The system of claim 8, wherein the first electrode is spaced apart from the second electrode by a second distance in a second direction, wherein the second distance is from about 2 mm to about 10 mm, and wherein the second direction is substantially perpendicular to the plane through the dielectric material layer.

10. A system for evaluating a bond, comprising:
 a first electrode;
 a second electrode;
 a dielectric material layer positioned at least partially between the first electrode and the second electrode, such that the second electrode is not in contact with the first electrode;
 a sacrificial material layer positioned in contact with a surface of a bonded structure that includes the bond, wherein the sacrificial material layer is positioned on a same side of the dielectric material layer as the second electrode and a different side of the dielectric material layer than the first electrode; and
 a power source configured to transmit an alternating current pulse to the first and second electrodes, which causes the first and second electrodes to generate an electrical arc that at least partially ablates a sacrificial material layer to generate a plasma, wherein the generation of the plasma generates a first wave that is directed into the bonded structure, and wherein the first wave reflects off of the bond in the bonded structure as a second wave.

11. The system of claim 10, further comprising a liquid positioned at least partially between the dielectric material layer and the sacrificial material layer, wherein the liquid directs a portion of the first wave toward the bond in the bonded structure.

12. The system of claim 10, wherein the system is able to generate the plasma and the first wave without using a laser.

13. The system of claim 10, wherein the first electrode is spaced apart from the second electrode by a first distance in a first direction, wherein the first distance is from about 0.5 mm to about 2 mm, wherein the first direction is substantially parallel to a plane through the dielectric material layer, wherein the first electrode is spaced apart from the second electrode by a second distance in a second direction, wherein the second distance is from about 2 mm to about 10 mm, wherein the second direction is substantially perpendicular to the plane through the dielectric material layer, and wherein the first electrode is positioned farther from the sacrificial material layer than the second electrode.

14. The system of claim 13, wherein the first electrode has a length in the first direction from about 10 mm to about 20 mm, and wherein the second electrode has a length in the first direction from about 1 mm to about 10 mm.

15. A method for evaluating a bond, comprising:
 placing a sacrificial material layer on a surface of a bonded structure; and
 generating an electrical arc to least partially ablate the sacrificial material layer, which generates a compression wave that is directed into the bonded structure, wherein the compression wave reflects off of the bond in the bonded structure as a tension wave.

16. The method of claim 15, further comprising inspecting the bond using an ultrasound imaging system after the compression wave reflects off of the bond.

17. The method of claim 15, wherein the electrical arc is generated using a first electrode, a second electrode, or both, and wherein a dielectric material layer is positioned between the first and second electrodes.

18. The method of claim 15, wherein ablating the sacrificial material layer generates a plasma, which generates the compression wave.

19. The method of claim 15, wherein a plasma is generated in response to the ablation of the sacrificial material layer, and wherein the plasma is positioned at least partially between a dielectric material layer and the sacrificial material layer.

20. The method of claim 15, wherein the compression wave is generated in response to the ablation of the sacrificial material layer.

* * * * *